US012329352B2

(12) United States Patent
Rauniyar et al.

(10) Patent No.: US 12,329,352 B2
(45) Date of Patent: Jun. 17, 2025

(54) SYSTEM, DEVICE AND METHOD FOR TURBIDITY ANALYSIS (71) Applicant: BOSTON SCIENTIFIC SCIMED, INC., Maple Grove, MN (US)

(72) Inventors: Niraj Prasad Rauniyar, Plymouth, MN (US); Robert J. Riker, Sewickley, PA (US); Timothy Paul Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 214 days.

(21) Appl. No.: 16/948,022

(22) Filed: Aug. 27, 2020

(65) Prior Publication Data
US 2021/0085165 A1    Mar. 25, 2021

Related U.S. Application Data (60) Provisional application No. 62/904,882, filed on Sep. 24, 2019.

(51) Int. Cl.
*A61B 1/00* (2006.01)
*A61B 1/05* (2006.01)
(Continued)

(52) U.S. Cl.
CPC .. *A61B 1/000094* (2022.02); *A61B 1/000096* (2022.02); *A61B 1/05* (2013.01);
(Continued)

(58) Field of Classification Search
CPC ... A61B 1/00009; A61B 1/00045; A61B 1/05; A61B 1/12; A61B 1/125; A61B 1/126;
(Continued)

(56) References Cited

U.S. PATENT DOCUMENTS

2006/0069306 A1    3/2006  Banik et al.
2008/0243054 A1*  10/2008  Mollstam ............. A61M 3/022
                                                        604/31
(Continued)

FOREIGN PATENT DOCUMENTS

CN    106455941 A    2/2017
CN    108292366 A    7/2018
(Continued)

OTHER PUBLICATIONS

Office Action in Chinese Application No. 202080066581.2, dated Oct. 22, 2024 (7 pages).
(Continued)

*Primary Examiner* — Aaron B Fairchild
*Assistant Examiner* — Stephen Floyd London
(74) *Attorney, Agent, or Firm* — Bookoff McAndrews, PLLC (57) ABSTRACT

An endoscopic system includes an endoscopic imager configured to capture images of a target site within a living body and a processor configured to determine one or more image metrics for each one of a plurality of image frames captured over a time span, analyze changes in the image metrics over the time span, and determine a turbidity metric for the target site based on the analyzed changes in the image metrics.

20 Claims, 4 Drawing Sheets (51) Int. Cl.
*A61M 3/02* (2006.01)
*G06T 5/00* (2024.01)
*G06T 7/00* (2017.01)
*G06V 20/20* (2022.01)
*G06V 40/10* (2022.01)

(52) U.S. Cl.
CPC ............ *A61M 3/0204* (2014.02); *G06T 5/00* (2013.01); *G06T 7/0012* (2013.01); *G06V 20/20* (2022.01); *G06V 40/10* (2022.01); *A61M 2205/331* (2013.01); *A61M 2205/3334* (2013.01); *G06T 2207/10024* (2013.01); *G06T 2207/10068* (2013.01); *G06V 2201/03* (2022.01)

(58) Field of Classification Search
CPC ....... A61B 1/307; A61B 3/0204; A61B 1/015; A61M 2205/334; A61M 2205/331; A61M 2205/3334; G06T 7/0012; G06T 2207/10024; G06T 2207/10068; G06T 2207/30084; G06T 7/0014; G06T 7/0016; G06T 2207/30168; G06V 20/698; G06V 2201/034
See application file for complete search history.

(56) References Cited

U.S. PATENT DOCUMENTS

| | | | |
|---|---|---|---|
| 2008/0273787 A1* | 11/2008 | Ducksbury | G06T 7/90 382/133 |
| 2009/0171148 A1* | 7/2009 | Lu | A61B 5/14539 600/109 |
| 2010/0280314 A1 | 11/2010 | Brommersma | |
| 2011/0237880 A1* | 9/2011 | Hamel | A61B 1/045 600/104 |
| 2012/0057754 A1 | 3/2012 | Dunton et al. | |
| 2012/0316421 A1* | 12/2012 | Kumar | A61B 1/00009 600/407 |
| 2013/0243286 A1* | 9/2013 | Radeva | G06K 9/00536 382/128 |
| 2015/0016700 A1* | 1/2015 | Drozdzal | A61B 1/00045 382/128 |
| 2018/0082104 A1 | 3/2018 | Wan et al. | |
| 2018/0177561 A1* | 6/2018 | Mintz | A61B 5/062 |
| 2018/0192982 A1* | 7/2018 | Pereira | A61B 1/307 |
| 2018/0271615 A1* | 9/2018 | Mahadik | A61B 1/3132 |
| 2018/0361055 A1 | 12/2018 | Pereira et al. | |
| 2019/0192237 A1 | 6/2019 | Harrah et al. | |
| 2020/0164118 A1* | 5/2020 | Woloszko | A61M 3/0258 |
| 2020/0367913 A1* | 11/2020 | Forstein | A61B 34/20 |
| 2022/0265121 A1* | 8/2022 | Fouts | A61B 1/317 |
| 2022/0287725 A1* | 9/2022 | Watanabe | A61B 17/1626 |

FOREIGN PATENT DOCUMENTS

| | | |
|---|---|---|
| JP | H0385173 A | 4/1991 |
| JP | 2004089684 A | 3/2004 |
| JP | 2014061132 A | 4/2014 |
| JP | 2017529132 A | 10/2017 |
| WO | 2018198255 A1 | 11/2018 |

OTHER PUBLICATIONS

Office Action in Japanese Application No. 2023-109724, dated Jun. 17, 2024 (3 pages).

* cited by examiner

SYSTEM, DEVICE AND METHOD FOR TURBIDITY ANALYSIS

PRIORITY CLAIM

The present disclosure claims priority to U.S. Provisional Patent Application Ser. No. 62/904,882 filed Sep. 24, 2019; the disclosure of which is incorporated herewith by reference.

FIELD

The present disclosure relates to a system, a device and a method for performing an endoscopic procedure and, in particular, a turbidity analysis of an endoscopic imaging environment.

BACKGROUND

An endoscopic imager may be used during a variety of medical interventions. The view of the anatomy provided by the imager is limited when the imaging environment is cloudy, or turbid. Turbidity may be caused by blood, urine or other particles. In some endoscopic procedures (e.g., ureteroscopic procedures), a turbid imaging environment may be managed by a fluid management system that circulates fluid in the imaged cavity.

SUMMARY

The present disclosure relates to an endoscopic system which includes an endoscopic imager configured to capture image frames of a target site within a living body; and a processor. The processor is configured to: determine one or more image metrics for each one of a plurality of image frames captured over a time span; analyze changes in the image metrics over the time span; and determine a turbidity metric for the target site based on the analyzed changes in the image metrics.

In an embodiment, the image metrics are image entropy metrics including a red entropy metric and a cyan entropy metric.

In an embodiment, the processor is further configured to: estimate a blood content in a current image frame; and alter the current image frame to mitigate a visual effect of the blood content and enhance a remainder of the current image frame.

In an embodiment, the processor is further configured to: identify and classify a particle in a current image frame.

In an embodiment, the endoscopic system further includes a display configured to annotate the current image frame with the turbidity metric.

In an embodiment, the display is further configured to: bracket the identified particle; and annotate the current image frame with the particle classification.

In an embodiment, the identified particle is a kidney stone and the classification relates to a size of the kidney stone.

The present disclosure also relates an endoscopic system which includes an endoscopic imager configured to capture image frames of a target site within a living body; a fluid delivery mechanism providing irrigation fluid to the target site for clarifying a field of view of the endoscopic imager; a processor configured to: determine a turbidity metric for at least one image from the imager; determine a fluid delivery adjustment for the irrigation fluid based on the turbidity metric; and control the fluid delivery mechanism to adjust a fluid delivery provided by the fluid delivery mechanism based on the determined fluid delivery adjustment.

In an embodiment, the processor is further configured to: determine a type of interventional activity based on a feature detection identifying an intervention instrument.

In an embodiment, the processor is further configured to: determine a phase of the interventional activity; and adjust the fluid delivery provided by the fluid delivery mechanism based on the phase of the interventional activity.

In an embodiment, the processor is further configured to: identify and classify a particle in a current image frame; and adjust the fluid delivery provided by the fluid delivery mechanism based on the particle classification.

In an embodiment, the particle is a kidney stone and the particle classification relates to a size of the kidney stone.

In an embodiment, the processor is further configured to: determine a blood metric for the at least one image; and adjust the fluid delivery provided by the fluid delivery mechanism based on the blood metric.

In an embodiment, the processor is further configured to: determine image entropy metrics for the at least one image.

In an embodiment, the turbidity metric and the blood metric are determined based in part on the image entropy metrics.

In addition, the present disclosure relates a method which includes determining one or more image metrics for each one of a plurality of image frames of a target site within a living body captured over a time span; analyzing changes in the image metrics over the time span; and determining a turbidity metric for the target site based on the analyzed changes in the image metrics.

In an embodiment, the image metrics are image entropy metrics including a red entropy metric and a cyan entropy metric.

In an embodiment, the method further includes estimating a blood content in a current image frame; and altering the current image frame to mitigate a visual effect of the blood content and enhance a remainder of the current image frame.

In an embodiment, the method further includes identifying and classifying a particle in a current image frame.

In an embodiment, the method further includes annotating the current image frame with the turbidity metric.

BRIEF DESCRIPTION

DETAILED DESCRIPTION

The present disclosure may be further understood with reference to the following description and the appended drawings, wherein like elements are referred to with the same reference numerals. The exemplary embodiments describe algorithmic improvements for managing turbidity in an endoscopic imaging environment. Typical urological procedures utilize an imaging device (e.g. a ureteroscope or other endoscopic imager), a mechanism to provide fluid (for clearing field of view and/or distending the body cavity) and a treatment mechanism (e.g. the Boston Scientific Litho-Vue™ device, and/or a source of laser or RF energy, etc.).

The improvements described herein include, e.g., methods for analyzing endoscopic images and determining turbidity and providing the information to a fluid management system to manage clarity in the field of view. Other improvements include algorithmically subtracting blood features from an endoscopic image and amplifying blood-obscured image features, particularly for urological procedures. Some common urological procedures include kidney stone management (e.g., lithotripsy), BPH (i.e., benign prostate hyperplasia) procedures (e.g., GreenLight™ laser surgery), prostatectomy, bladder tumor resection, uterine fibroids management, diagnostics, etc. although those skilled in the art will understand that the devices and techniques for improving images may be used in a wide variety of procedures (i.e., non-urological procedures as well) in which turbidity is an issue.

Figure 1:
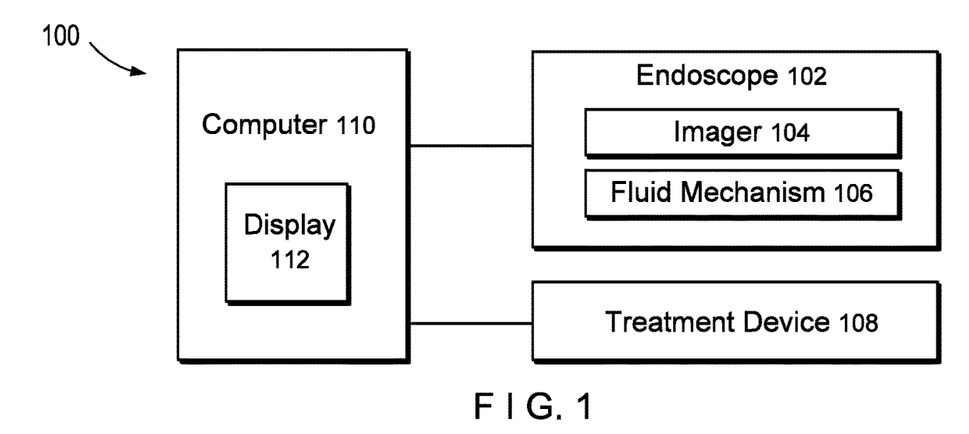
FIG. 1 shows a system for performing an endoscopic procedure according to various exemplary embodiments of the present disclosure.

FIG. 1 shows a system 100 for performing an endoscopic procedure according to various exemplary embodiments of the present disclosure. The system 100 includes an endoscope 102 with an imager 104 for acquiring image frames of an anatomical site within a living body during the endoscopic procedure and a fluid delivery mechanism 106 for providing a fluid (e.g., saline), to the anatomy to clear blood and debris that may impair the view of the imager 104. The fluid delivery mechanism 106 also provides suction to simultaneously remove fluid from the anatomy. In this way, the anatomy is continuously refreshed with substantially transparent fluid such that clearer images may be generated.

The system 100 may further include a treatment device 108, selected depending on the nature of the endoscopic procedure. The treatment device 108 may be run through the endoscope 102 or may be external to the endoscope 102. For example, the treatment device 108 may be, e.g., a laser or a shockwave generator for breaking up kidney stones or a resectoscope for removing prostate tissue. When the endoscopic procedure is for diagnostic purposes, i.e., for examining the anatomy and not for treating a condition, there may be no treatment device used. Although the exemplary embodiments are described with respect to urological imaging, the exemplary embodiments are not limited thereto. Certain embodiments may be applicable as well to a wide range of procedures such as, for example, endoscopic procedures in the digestive system, etc., including endoscopic procedures that do not include a fluid delivery mechanism.

The system 100 includes a computer 110 processing image frames provided by the imager 104 and providing the processed images to a display 112. The computer 110 and the display 112 are provided, in this embodiment, at an integrated station such as an endoscopic console. Other features for performing the urological procedure may be implemented at the endoscopic console, including, e.g., actuators controlling a flow rate, pressure or manner of dispensation for the fluid delivered through the fluid delivery mechanism 106. The exemplary embodiments describe algorithmic processes for altering and enhancing the displayed images, generally on a continuous basis or in any other desired manner.

In one embodiment, image metrics determined from captured image frames are used to estimate a degree to which a video sequence is being occluded by a turbid imaging environment. The image metrics include image entropy metrics. Image entropy may be generally defined as a measure of information content in an image, which may be approximated by evaluating a frequency of intensity values in an image. High entropy may reflect, e.g., a high amount of anatomic detail associated with a clear image, or it may reflect, e.g., a swirling cloud of particles obscuring the anatomy and will be associated with a non-clear image. A time course of entropy measurements may help differentiate between e.g. a high entropy clear image and a high entropy non-clear image. For example, the time course of entropy measurements for a series of images may differentiate between these two types of images through a variability of entropy in non-clear images.

Alternatively, low entropy may reflect a loss of contrast and/or the obscuring of detail. Low entropy may also result from a very plain scene (e.g., a blank white wall). An amount of image entropy may be measured with image entropy metrics including, e.g. a total entropy in an image or a ratio of red entropy to cyan entropy in an image. In an embodiment, the ratio of red entropy to cyan entropy may highlight a contribution of blood (represented by red entropy) versus other fluids (represented by cyan entropy) to highlight the blood contribution. In some embodiments, the image entropy metrics may further encompass entropy fluctuations in specific temporal frequency bands in a sequence of images. As described above, the entropy fluctuations are measured over time to differentiate between clear and non-clear images. Specifically, a rapid change in a high entropy measure of an observed image may reflect chaotic entropy associated with a swirling cloud of particles, thus signifying that the observed image is a non-clear image.

An optical flow analysis is utilized to characterize a changing scene between images. The optical flow analysis generally identifies neighborhoods in a given image that may correspond to neighborhoods in a prior image and identify differences in their positions. One such algorithm for estimating such positional displacement is the Farneback algorithm. Such an analysis provides information about stationary and moving objects in the field, as well as systematic field motion, i.e., pan, rotation, advancement and retraction of the camera.

Machine learning systems may also be employed to characterize and classify video segments according to a level of occlusion and scene contents. For example, machine learning methods such as neural networks, convolutional neural networks, optimizers, linear regression and/or logistical regression classifiers may be used to discover novel image analyses and/or combinations of the above-described entropy metrics to characterize and classify the video segments. The machine learning methods may generate scalar estimates of turbidity, as well as blood and particle-field probability.

In another embodiment, other metrics may be used for classifying the video segments such as, for instance, spatial and temporal frequency decompositions. A spatial frequency analysis may effectively measure a sharpness of an image to provide direct insight into image clarity. An image with a turbid field of particles may present relatively high spatial frequencies, the spatial frequencies being similar to spatial frequencies of an image with high anatomic detail. Distinguishing between the high spatial frequencies of the image with the turbid field and the image with high anatomic detail may be done with a temporal frequency analysis. As described above, the temporal frequency analysis refers to tracking changes of the metrics over time.

The machine learning systems may optimize the non-linear combiners and various assessments including a particle/stone assessment, a blood assessment, and a clarity assessment, to be described in detail below. Various metrics may be derived through a linear combination of pixel values, intensity histogram values, non-linear functions (e.g., logarithms) of the above, and time-course sequences of these values. The machine learning systems may use algorithms to find alternative combinations of the above values that do not directly correspond to spatial frequency or entropy, but more effectively correspond to an observer's impression of turbidity.

The machine learning systems operate on a feature space that they are presented with (i.e., values of the systems determine classification). In an embodiment, video machine learning systems have video pixels inputted directly into the systems. The image metrics (e.g., spatial frequency spectra) are computed from these values in common machine learning models. The feature space may be augmented by feeding system analyses that may be helpful but not well-suited for computation in the machine learning systems. Entropy, for example, believed to be useful for this calculation, is not readily computable on many common video processing neural network architectures. As a result, the machine learning systems may perform better when provided with, in addition to the raw pixels, other analyses. Feeding a neural network with the intensity histogram data, including logarithms thereof, allow the network to incorporate entropy and entropy-like measures, thereby converging more quickly on a better result. Mathematical variations of the metrics may be identified by the system as superior. Thus, careful enrichment of the feature space may improve performance dramatically.

No particular metric directly derivable from image data does a suitable job, in itself, estimating turbidity in a clinical setting with a constantly changing image background. The exemplary embodiments describe methods for e.g. informing and tuning a neural network with entropy-related metrics to assess a turbidity level from image data.

The aforementioned metrics and analyses may be input into an appropriately designed machine learning algorithm that performs a plurality of assessments that may be output to a display to annotate a displayed image frame and/or may inform further analyses.

In a first example, a particle or stone assessment is performed. The particle/stone assessment determines properties for particles suspended in the fluid. Feature detection may be used to determine the nature of the particles. For instance, a kidney stone may be identified as such and metrics such as a size of the stone may be determined, as well as a depth estimation (i.e., a distance from imager). Motion of the stone may also be estimated, based in part on the aforementioned optical flow analysis. Other particles may include, e.g., proteins, tissue, a protrusion, a thrombus, etc. The particle/stone assessment identifies the particle, segments it in the image frame, and sizes it.

The particle identification and classification may be used to annotate the current image frame. For instance, the particle may be bracketed and associated metrics displayed to inform the operating physician and allow for quicker decision making. The particle/stone analysis may also be used to manage the delivery of irrigating fluid via by the fluid delivery mechanism 106. For example, whereas typically a turbid field may suggest a need to increase fluid flow, an identification of a mobile stone may suggest a reduction in the fluid flow to maintain the position of the stone in the imager field of view. Additionally, the particle/stone assessment may impact the use of the treatment device 108, depending on the nature of the treatment, either directly or indirectly. For example, in a lithotripsy procedure, the classification of a stone as, e.g., too large to retrieve, too large to pass naturally, or small enough to pass naturally, may automatically (or under physician guidance) drive or influence the operation of the system during the remainder of the intervention.

In a second example, a clarity assessment is performed. The clarity assessment determines a total measure of turbidity in the image. As discussed previously, the machine learning processes utilizing, e.g. image entropy metrics as an input, may produce a novel turbidity measure. The turbidity measure may be e.g. a scalar estimate of turbidity or some other metric developed by the machine learning algorithms. The clarity assessment may be used to annotate a currently displayed image and may also be used to manage the delivery of irrigating fluid.

In a third example, a blood assessment is performed. The blood assessment estimates a total measure of blood content in the cavity in, for instance, parts-per-million (PPM), although other metrics may be used. The blood assessment may be used to annotate a currently displayed image and may also be used to manage the delivery of irrigating fluid. In addition, the blood assessment may inform, e.g., a thrombus analysis, laser settings for e.g. a BPH procedure, etc.

A fourth assessment, in addition to the particle assessment, clarity assessment, and blood assessment discussed above, may be used to manage fluid circulation in the imaged cavity in vivo. The fourth assessment relates to the type of intervention being performed during the endoscopic procedure. For example, the intervention may be kidney stone management, prostatectomy, uterine fibroids management, etc. A feature detector may be applied to a current image frame to determine the type of interventional activity underway. For instance, during a laser prostatectomy, the laser device will be within the FOV of the imager and may be identifiable as a laser device by a feature detector.

In another example, a stone retrieval basket device may be identified by a feature detector, etc. Once identified, the phase of the intervention is assessed. For example, the system could measure the extent to which a stone has been pulverized or otherwise reduced in size and/or could determine when a stone has been received within a basket for retrieval, etc. Thus, the interventional assessment may be used in combination with, e.g., at least the particle/stone assessment during a laser lithotripsy procedure, to identify phases of the intervention (e.g., no stones in field, stones in field, lasering in progress) that may influence desired flow characteristics. The type of intervention may affect the optimal flow rate of the fluid of the irrigation system. For instance, a laser prostatectomy may demand a higher flow rate than, e.g., a kidney stone procedure due to the heating of the tissue. The heating of the tissue may cause a complementary heating of the fluid in the cavity. A more rapid inflow and outflow of fluid may act to maintain a more constant temperature in the cavity and prevent damage to healthy tissue.

Figure 2:
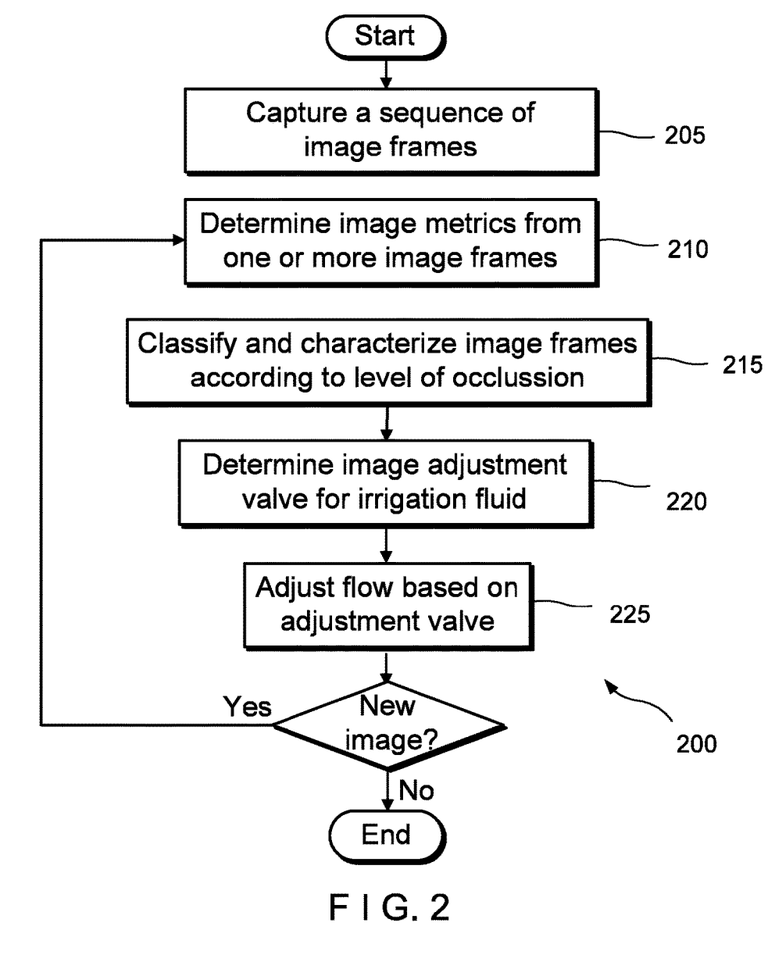
FIG. 2 shows a method for managing irrigation fluid flow in a closed-loop feedback system according to various exemplary embodiments of the present invention.

FIG. 2 shows a method 200 for managing irrigation fluid delivery in a closed-loop feedback system according to various exemplary embodiments of the present invention. The method 200 may employ some or all of the metrics described above. Certain of the described metrics may be derived from a single image frame, while others may be derived from a sequence of image frames. Thus, the closed-loop adjustment of the fluid delivery may be performed based on multiple image frames. However, considering the rapid frame rate of imagers typically used in the art, the fluid delivery adjustments are applied on a rapid enough basis that the adjustments will appear to be substantially continuous from the perspective of the operating physician.

In 205, a sequence of image frames is captured by the imager 104. As noted above, the total number of images necessary to perform a given calculation may vary, so the number of images in the sequence may vary accordingly.

In 210, some or all of the above-described metrics are determined from one or more image frames in the sequence. For example, image entropy metrics may be derived from each of the images and determined therefrom as the images are captured. In another example, pixel metrics are determined directly from the images.

In 215, the various metrics and analyses are processed with a machine-learning combiner algorithm/function to characterize and classify the images or video segments according to a level of occlusion and scene contents. As described above, the machine-learning algorithm may combine the metrics in various ways and self-adjust a weighting or use of a metric depending on the analyses discovered. It is noted that all of the aforementioned metrics/analyses with the exception of the therapy feature detection and interventional phase assessment are input to the machine-learning combiner algorithm, while the therapy feature/phase detection/assessment are determined directly from the image frames and do not inform the particle assessment, blood assessment or clarity assessment.

In 220, a flow management algorithm processes the particle assessment, blood assessment, clarity assessment and intervention phase assessment to determine whether a fluid delivery adjustment of the irrigation fluid is warranted, and if so, an adjustment value.

In 225, the adjustment value is fed back to the processor and the flow provided by the fluid delivery mechanism is adjusted.

The method steps 205-225 are performed on a substantially continuous basis, providing a closed-loop feedback system for managing fluid flow during an endoscopic intervention.

Figure 3:
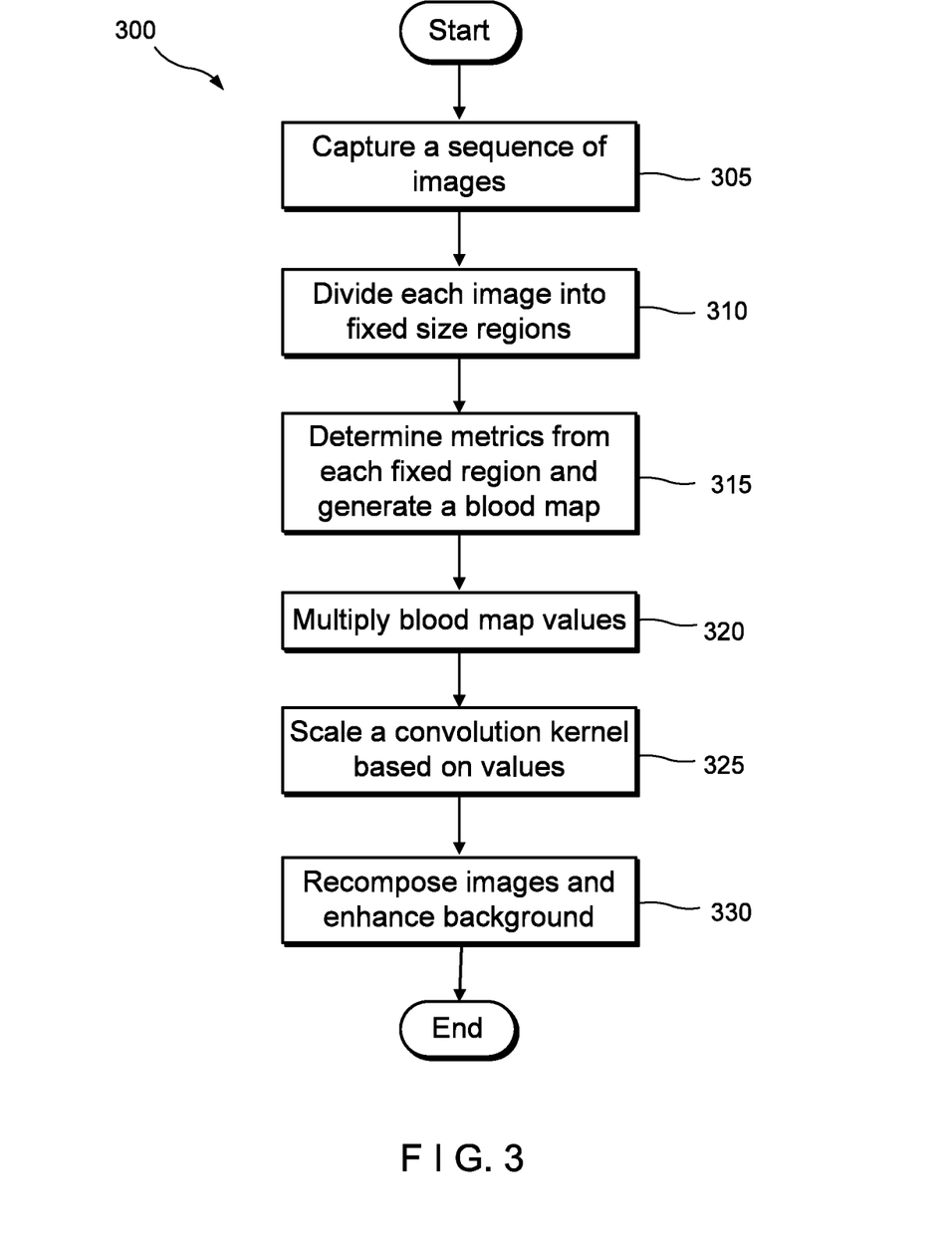
FIG. 3 shows a method for enhancing visibility through a liquid medium clouded by blood according to a first exemplary embodiment.
Figure 4:
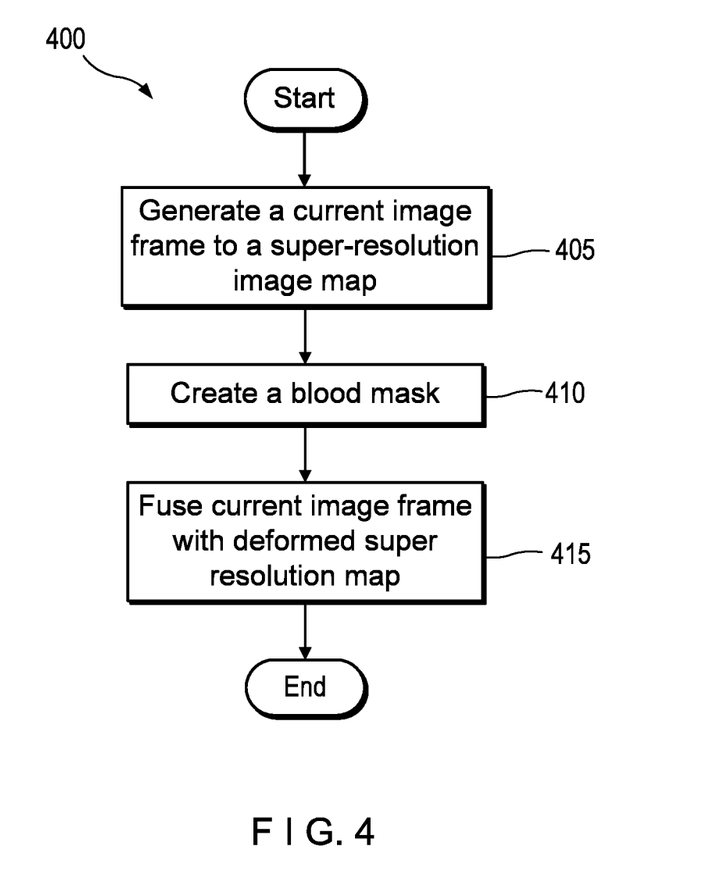
FIG. 4 shows a method for enhancing visibility through a liquid medium clouded by blood according to a second exemplary embodiment.

Certain of the above-described metrics, particularly relating to the blood assessment and the clarity assessment, may be used to algorithmically provide image enhancements to compensate for a bloody field of view in an endoscopic intervention. Turbidity caused by blood may be managed by algorithmically subtracting blood features from images and amplifying blood-obscured features. Methods 300 and 400, described below, may be applied alone or in combination.

FIG. 3 shows a method 300 for enhancing visibility through a liquid medium clouded by blood according to a first exemplary embodiment. The method 300 includes certain steps of the method 200 for managing irrigation fluid delivery (or steps similar to those of the method 200) and may be used alone or in combination therewith.

In 305, a sequence of images is captured by the imager 104 according to step 205 of method 200. In 310, each of the images is divided into fixed size regions. Each region may be, e.g., 20×20 pixels.

In 315, certain of the metrics described above are calculated and processed, with the aforementioned machine-learning combiner algorithms, for each of the regions, similar to steps 210-215 of method 200. In this way, each of the regions are assessed for blood content and a "blood map" is generated to characterize each of the regions according to a presence of blood. Specifically, the metrics informing the machine-learning combiner algorithms for the blood assessment are determined and processed to classify each of the regions. It is not necessary to perform the particle/stone assessment or the clarity assessment, or to determine any intervention device features for the method 300. However, in another embodiment, where, e.g., a turbid field is caused by particles other than blood, the clarity assessment may be performed.

In 320, the blood map values are multiplied by regional frame-to-frame variations of each metric associated with blood detection in the combiner, as adjusted for optical flow. In this way, the individual image sub-regions may be utilized to localize the areas occluded by blood and selectively or proportionally apply image enhancements to mitigate the loss of image detail caused by the blood.

In 325, the values resulting from 320 are used to scale a convolution kernel or color transform calculated to be complementary to each metric, which is then applied in its region with a sigmoid reduction at the region boundary. Entropy-related kernels will use either low-pass filter kernels (for positive entropy correlation) or high-pass filter kernels (for negative entropy correlation) applied to the associated color channels.

In 330, the image frames are recomposed from a spatial frequency representation for each of the regions, consisting of a phase and an altered magnitude, to deemphasize the bloody foreground and enhance the interesting background. The visual effect of the blood may be mitigated across the image to varying degrees depending on the scaling of the convolution kernel. The enhancement may be applied to the magnitude components of the spatial frequencies, which may then be recombined with their phase components and transformed back into a conventional image.

FIG. 4 shows a method 400 for enhancing visibility through a liquid medium clouded by blood according to a second exemplary embodiment.

In 405, a current image frame is correlated to a super-resolution image map using a deformable non-linear transform. The super-resolution image map may be generally defined as an improved resolution image generated from a fusion of lower-resolution images. A current image may be fused with the super-resolution image map to enhance the resolution of the current image.

In 410, a "blood mask" is created based on the aforementioned metrics associated with blood detection, the blood mask reflecting the spatial distribution of inferred blood turbidity in a given image frame.

In 415, the current image frame is fused with the deformed super-resolution map to generate an enhanced frame that is a weighted average of the current frame and the super-resolution map. The pixels are driven toward those of the original image frame when the blood mask value is low, and the pixels are driven toward those of the super-resolution map when the mask value is high.

Figure 5:
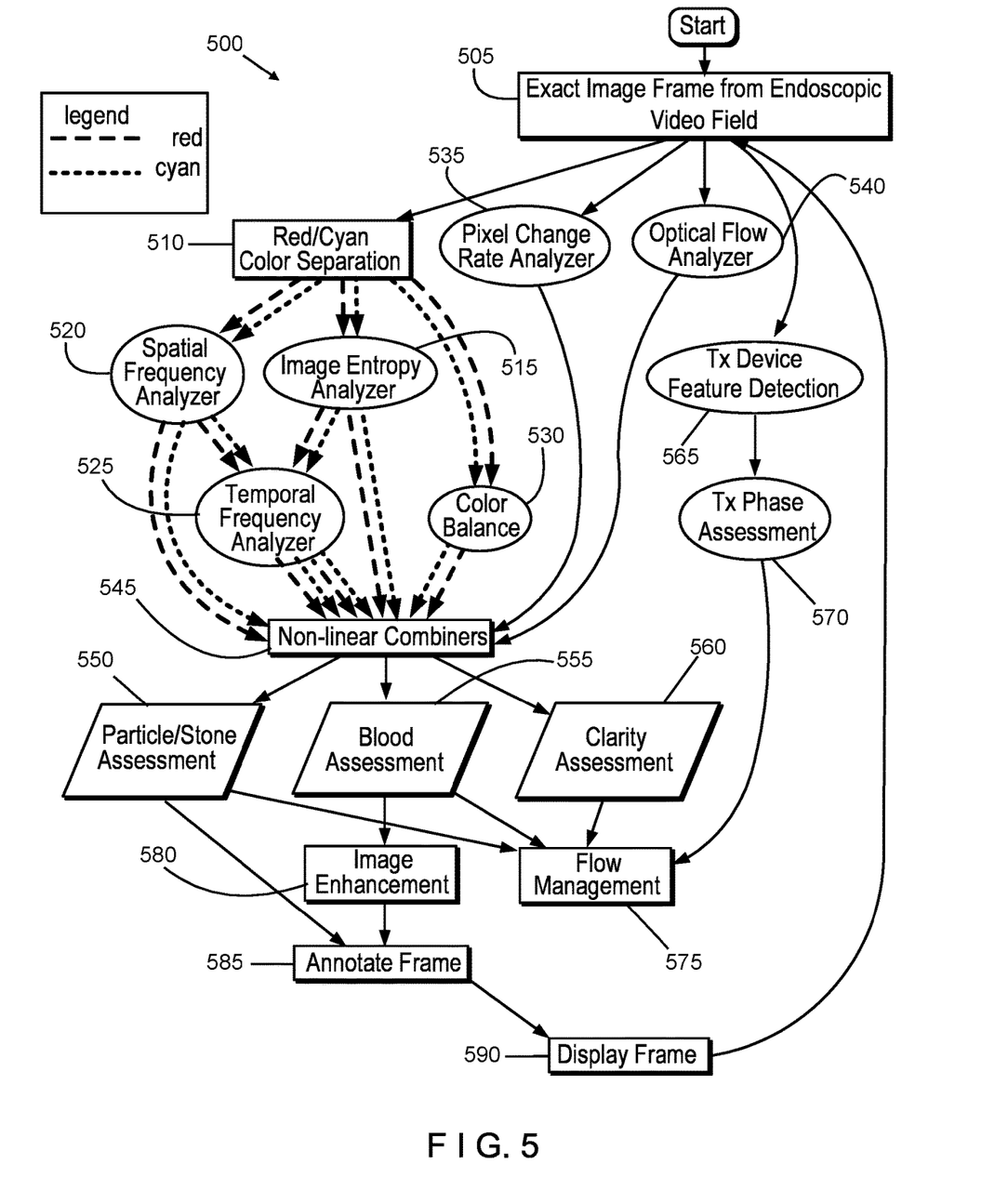
FIG. 5 shows a flowchart describing a combined embodiment of the methods of FIGS. 2-4.

FIG. 5 shows a flowchart 500 describing a combined embodiment comprising elements of methods 200, 300 and 400. It will be understood by those skilled in the art that the various metrics and analyses described previously may be used alone or in combination in a variety of ways.

In 505, an image is extracted from an endoscopic imaging feed. As discussed previously, certain of the metrics/analyses, such as e.g. the optical flow analysis, require a number of images to determine. However, it may be assumed for the purposes of the flowchart 500 that sufficient previous images have been captured to perform each of the calculations.

In 510, the image is separated into its red and cyan components for calculating various metrics. For example, in 515 the red and cyan entropy values are calculated. Metrics such as e.g. a red to cyan entropy ratio may be calculated, or the red cyan value may be used directly. In 520, the spatial frequency analysis is performed for the red and cyan spectra components. In 525, the red/cyan entropy values and the spatial frequency analysis inform a temporal frequency analysis. It will be understood by those skilled in the art that the temporal frequency analysis requires a sequence of pictures for analyzing differences therebetween. For example, entropy fluctuations are measured over time. In 530, a color balance is performed where the red and cyan components are compared. In 535, the pixel change rate analysis is performed where pixel values between images are compared. In 540, the optical flow analysis is performed for correlating successive images and deriving information such as e.g. object or tissue motion over time.

In 545, the aforementioned metrics/analyses are combined by a machine learning system in various ways to generate the particle information (particle/stone assessment 550), blood content information (blood assessment 555), and turbidity information (clarity assessment 560). An interventional assessment is also performed where an interventional feature in the image is identified (therapy device feature detection 565) and a phase of the intervention is assessed (therapy phase assessment 570). The particle, blood, clarity and interventional analyses are used to control a fluid flow 575 of the irrigation system. As discussed previously, the fluid flow management 575 may include adjusting a flow rate, a pressure, or a manner of dispensing the fluid.

In 580, the current image may be enhanced by removing or mitigating a blood component of the image according to methods 300 or 400. In 585, the current image may be annotated according to method 200. The current image may further be annotated with blood or turbidity metrics derived in the blood/clarity assessments. In 590, the enhanced/annotated image is displayed. As further images are captured the aforementioned steps/metrics/analysis are performed or determined.

In another embodiment, a computer-readable medium comprises instructions which, when executed by a computer, cause the computer to perform the various image processing steps/analyses discussed above, e.g., determining the turbidity metric.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. An endoscopic system, comprising:
an endoscopic imager configured to capture a plurality of image frames of a target site within a living body over a time span; and
a processor configured to:
determine one or more image metrics for each of a first image frame and a second image frame of the plurality of image frames captured over the time span;
compare the one or more image metrics of the first image frame to the one or more image metrics of the second image frame to determine changes in the one or more image metrics over the time span;
determine a turbidity metric for the target site based on the changes in the one or more image metrics;
identify, classify, and determine properties of a particle in a current image frame of the plurality of image frames; and
control a fluid delivery mechanism to provide fluid to the target site and adjust a fluid flow based on the identified particle, wherein the processor decreases the fluid flow when the identified particle is a kidney stone, and wherein the processor increases the fluid flow when the identified particle is associated with a turbid field.

2. The endoscopic system of claim 1, wherein the one or more image metrics comprises an image entropy metric including a ratio of a red entropy metric to a cyan entropy metric.

3. The endoscopic system of claim 2, wherein the processor is further configured to:
estimate a blood content in the current image frame; and
alter the current image frame to mitigate a visual effect of the blood content and enhance a remainder of the current image frame.

4. The endoscopic system of claim 1, further comprising:
a display configured to annotate the current image frame with the turbidity metric.

5. The endoscopic system of claim 4, wherein the display is further configured to:
bracket the identified particle; and
annotate the current image frame with the particle classification.

6. The endoscopic system of claim 5, wherein the identified particle is a kidney stone and the classification relates to a size of the kidney stone.

7. The endoscopic system of claim 1, wherein the one or more image metrics comprises an image entropy metric, and wherein the processor is further configured to measure fluctuations in the image entropy metric in the plurality of image frames to distinguish between a high entropy non-clear image and a high entropy clear image in the plurality of image frames.

8. The endoscopic system of claim 1, wherein the processor is further configured to perform an optical flow analysis on the plurality of image frames.

9. An endoscopic system, comprising:
an endoscopic imager configured to capture a plurality of image frames of a target site within a living body over a time span;
a fluid delivery mechanism configured to deliver irrigation fluid to the target site for clarifying a field of view of the endoscopic imager; and
a processor configured to:
track changes in one or more image metrics in the plurality of image frames by comparing the one or more image metrics over the time span, image frame by image frame;
determine a turbidity metric for at least one image frame of the plurality of image frames based on the changes;
identify, classify, and determine properties of a particle in a current image frame of the plurality of image frames;
determine a fluid delivery adjustment for the irrigation fluid based on the turbidity metric and the identified particle; and
control the fluid delivery mechanism to adjust a fluid delivery provided by the fluid delivery mechanism based on the determined fluid delivery adjustment, wherein the processor decreases the fluid delivery when the identified particle is a kidney stone, and wherein the processor increases the fluid delivery when the identified particle is associated with a turbid field.

10. The endoscopic system of claim 9, wherein the processor is further configured to:
determine a type of interventional activity based on a feature detection identifying an intervention instrument.

11. The endoscopic system of claim 10, wherein the processor is further configured to:
determine a phase of the type of interventional activity; and
adjust the fluid delivery provided by the fluid delivery mechanism based on the phase of the type of interventional activity.

12. The endoscopic system of claim 9, wherein the processor is further configured to:
adjust the fluid delivery provided by the fluid delivery mechanism based on the particle classification.

13. The endoscopic system of claim 12, wherein the particle is a kidney stone and the particle classification relates to a size of the kidney stone.

14. The endoscopic system of claim 9, wherein the processor is further configured to:
determine a blood metric for the current image frame; and
adjust the fluid delivery provided by the fluid delivery mechanism based on the blood metric.

15. The endoscopic system of claim 14, wherein the processor is further configured to:
determine image entropy metrics for the current image frame.

16. The endoscopic system of claim 15, wherein the turbidity metric and the blood metric are determined based in part on the image entropy metrics.

17. The endoscopic system of claim 9, wherein the one or more image metrics comprises an image entropy metric including a ratio of a red entropy metric to a cyan entropy metric.

18. A method for analyzing images of a target site within a living body using an endoscopic imager and a processor, the endoscopic imager being configured to capture a plurality of image frames of the target site within the living body over a time span, the method comprising:
determining, via the processor, one or more image metrics for a first image frame and a second image frame of the plurality of image frames, wherein the one or more image metrics comprises an image entropy metric;
comparing, via the processor, the one or more image metrics of the first image frame and the second image frame to determine changes in the one or more image metrics;
determining, via the processor, a turbidity metric for the target site based on the changes;
identifying, classifying, and determining, via the processor, properties of a particle in a current image frame of the plurality of image frames; and
measuring, via the processor, fluctuations in the image entropy metric in the plurality of image frames to distinguish between a high entropy non-clear image and a high entropy clear image in the plurality of image frames.

19. The method of claim 18, further comprising:
estimating a blood content in the current image frame; and
altering the current image frame to mitigate a visual effect of the blood content and enhance a remainder of the current image frame.

20. The method of claim 18, further comprising:
annotating the current image frame with the turbidity metric.

* * * * *